US011420028B2

(12) United States Patent
Koike

(10) Patent No.: US 11,420,028 B2
(45) Date of Patent: Aug. 23, 2022

(54) GUIDE WIRE

(71) Applicant: ASAHI INTECC CO., LTD., Aichi (JP)

(72) Inventor: Tadahiro Koike, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 317 days.

(21) Appl. No.: 16/745,368

(22) Filed: Jan. 17, 2020

(65) Prior Publication Data

US 2020/0164183 A1   May 28, 2020

Related U.S. Application Data

(63) Continuation of application No. PCT/JP2017/026012, filed on Jul. 19, 2017.

(51) Int. Cl.
*A61M 25/09* (2006.01)

(52) U.S. Cl.
CPC ... *A61M 25/09* (2013.01); *A61M 2025/09066* (2013.01); *A61M 2025/09191* (2013.01)

(58) Field of Classification Search
CPC ........ A61M 25/09; A61M 2025/09066; A61M 2025/09191; A61M 2025/09083; A61M 2025/09175; A61M 2025/09108; A61M 2025/09133; A61B 17/22; A61B 2017/22038
See application file for complete search history.

(56) References Cited

U.S. PATENT DOCUMENTS

| | | | | | |
|---|---|---|---|---|---|
| 5,165,421 | A | * | 11/1992 | Fleischhacker | A61B 17/3207 138/130 |
| 5,725,534 | A | * | 3/1998 | Rasmussen | A61B 17/12022 600/585 |
| 6,387,060 | B1 | * | 5/2002 | Jalisi | A61M 25/0043 600/585 |
| 2001/0021831 | A1 | * | 9/2001 | Fleischhacker | A61M 25/0105 604/264 |
| 2008/0146967 | A1 | * | 6/2008 | Richardson | A61L 31/18 600/585 |
| 2009/0112126 | A1 | * | 4/2009 | Keating | A61M 25/09 600/585 |

(Continued)

FOREIGN PATENT DOCUMENTS

| CN | 104784807 A | 7/2015 |
|---|---|---|
| EP | 2 865 407 A1 | 4/2015 |

(Continued)

OTHER PUBLICATIONS

International Search Report issued in International Application PCT/JP2017/026012 dated Aug. 29, 2017.

*Primary Examiner* — Sean P Dougherty
(74) *Attorney, Agent, or Firm* — Xsensus LLP

(57) ABSTRACT

A guide wire that includes a core shaft that is made of a first material, a coil that is provided to cover an outer periphery of the core shaft and is formed by twisting a first wire made of the first material and a plurality of second wires made of a second material different from the first material, and a distal end joint that joints a distal end of the core shaft and a distal end of the coil, and the distal end joint is made of the first material and is continuous from the distal end of the core shaft and the distal end of the first wire, and the distal end joint wraps the distal ends of the plurality of second wires.

10 Claims, 3 Drawing Sheets

(56) References Cited

U.S. PATENT DOCUMENTS

| | | | |
|---|---|---|---|
| 2009/0112127 A1* | 4/2009 | Keating | A61M 25/09 600/585 |
| 2012/0029476 A1 | 2/2012 | Kanazawa | |
| 2015/0119757 A1 | 4/2015 | Sato et al. | |
| 2015/0119861 A1* | 4/2015 | Miyata | A61M 25/09 604/528 |
| 2015/0206622 A1 | 7/2015 | Murata et al. | |
| 2015/0238735 A1 | 8/2015 | Furukawa et al. | |
| 2018/0235442 A1 | 8/2018 | Yamanaka | |

FOREIGN PATENT DOCUMENTS

| | | |
|---|---|---|
| JP | 4785170 B | 7/2011 |
| JP | 2012-029978 A | 2/2012 |
| JP | 2014-161705 A | 9/2014 |
| JP | 2015-083086 A | 4/2015 |
| JP | 2015-137428 A | 7/2015 |
| JP | 2015-159865 A | 9/2015 |
| JP | 2017-099577 A | 6/2017 |
| WO | 99/29260 A2 | 6/1999 |
| WO | 2017/077626 A1 | 5/2017 |

* cited by examiner

GUIDE WIRE

CROSS REFERENCES TO RELATED APPLICATIONS

This application is a bypass continuation of International Application No. PCT/JP2017/026012, filed Jul. 19, 2017, the entire contents of which are incorporated herein by reference.

TECHNICAL FIELD

The present disclosure relates to a guide wire.

BACKGROUND

When treating a stenosis that occurs in blood vessels such as coronary arteries surrounding the heart, or when treating a region where the blood vessel is completely occluded due to the progress of calcification (for example, chronic total occlusion: CTO), a guide wire for guiding a treatment instrument such as a balloon catheter is inserted into the blood vessel, prior to the treatment instrument.

The guide wire requires high flexibility and good resiliency of the distal end portion. For example, there is proposed the guide wire in which the coil distal end is jointed to the outer periphery of the distal end of a core shaft by welding, and a reinforcing portion is welded to the distal end of the core shaft (see Patent Literature 1, for example).

CITATION LIST

Patent Literature

Patent Literature 1: Japanese Patent No. 4785170

SUMMARY

The present application provides a guide wire, comprising: a core shaft that is made of a first material; a coil that is provided to cover an outer periphery of the core shaft and is formed by twisting a first wire made of the first material and a plurality of second wires made of a second material different from the first material; and a distal end joint that joints a distal end of the core shaft and a distal end of the coil, wherein the distal end joint is made of the first material and is continuous from the distal end of the core shaft and the distal end of the first wire, and the distal end joint wraps the distal ends of the plurality of second wires.

DETAILED DESCRIPTION

Technical Problem

Figure 1:
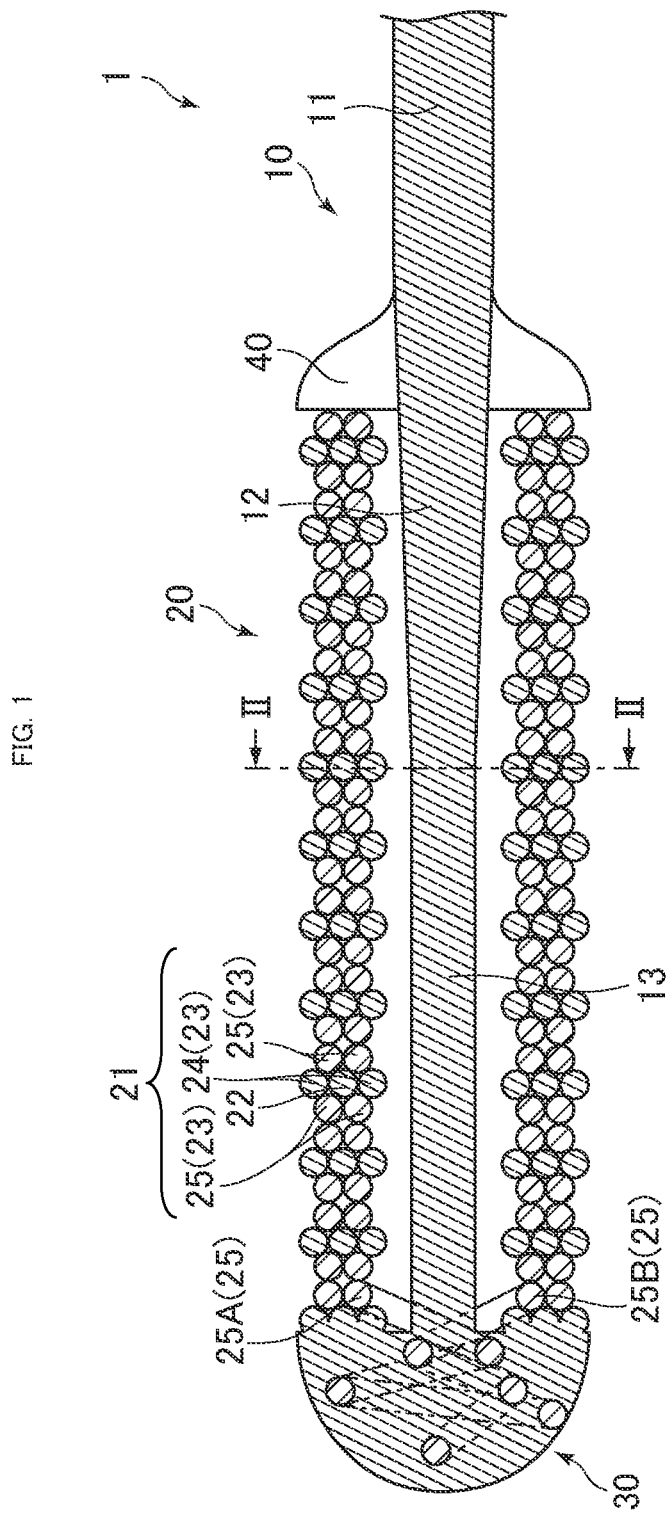
FIG. 1 illustrates a schematic cross-sectional view of a guide wire according to an embodiment of the present disclosure.

However, in the case of the above-described conventional guide wire, there is a possibility that the coil body is detached from the distal end joint part during the operation of the guide wire.

The present disclosure has been made on the basis of the above circumstances, and aims at providing a guide wire capable of preventing the coil body from being detached from the distal end joint part during operation.

Solution to Problem

To solve the above-described problem, a guide wire according to an aspect of the disclosure includes a core shaft that is made of a first material, a coil body that is provided to cover an outer periphery of the core shaft and is formed by twisting a first element wire made of the first material and a plurality of second element wires made of a second material different from the first material, and a distal end joint part that joints a distal end of the core shaft and a distal end of the coil body, in which the distal end joint part is made of the first material and is continuous from the distal end of the core shaft and the distal end of the first element wire, and the distal end joint part wraps the distal ends of the plurality of second element wires.

Here, the melting point of the second material may be higher than the melting point of the first material.

Moreover, the plurality of second element wires may include the 2-1 wire and the 2-2 wire. The 2-1 wire may extend spirally at the distal end joint part so as to broaden radially outward toward the distal end, and the 2-2 wire may extend spirally at the distal end joint part so as to narrower radially inward toward the distal end.

Note that in the specification, "distal end direction" is a direction along the axial direction of the guide wire, and indicates a direction of the side on which the distal end joint part is positioned relative to the core shaft. The "rear end direction" is a direction along the axial direction of the guide wire, and indicates the direction opposite to the distal end direction.

Advantageous Effects of Disclosure

The present disclosure can provide a guide wire capable of preventing the coil body from being detached from the distal end joint part during operation.

Hereinafter, one embodiment of the present disclosure is described with reference to drawings. However, the present disclosure is not limited only to the embodiment illustrated in the drawings.

FIG. 1 illustrates a schematic cross-sectional view of a guide wire 1 according to an embodiment of the present disclosure.

As illustrated in FIG. 1, the guide wire 1 roughly includes a core shaft 10, a coil body 20, a distal end joint part 30, and a proximal end fixing part 40.

The core shaft 10 includes a core shaft main body 11, a tapered portion 12, and a distal end portion 13. The tapered portion 12 extends continuously from the core shaft body 11 so as to reduce in diameter toward the distal end. The distal end portion 13 extends continuously from the tapered portion 12 toward the distal end. Note that the rotation operation and the like of the guide wire 1 by a user are performed in the edge part of the rear end side of the core shaft main body 11.

The material forming the core shaft 10 is not particularly limited as long as the distal end portion 13 and the tapered portion 12 have flexibility and have antithrombogenicity and biocompatibility. For example, it is possible to adopt stainless steel, a superelastic alloy such as a Ni—Ti alloy, or the like. Note that the material forming the core shaft 10 is the first material.

Next, the coil body 20 will be described.

Figure 2:
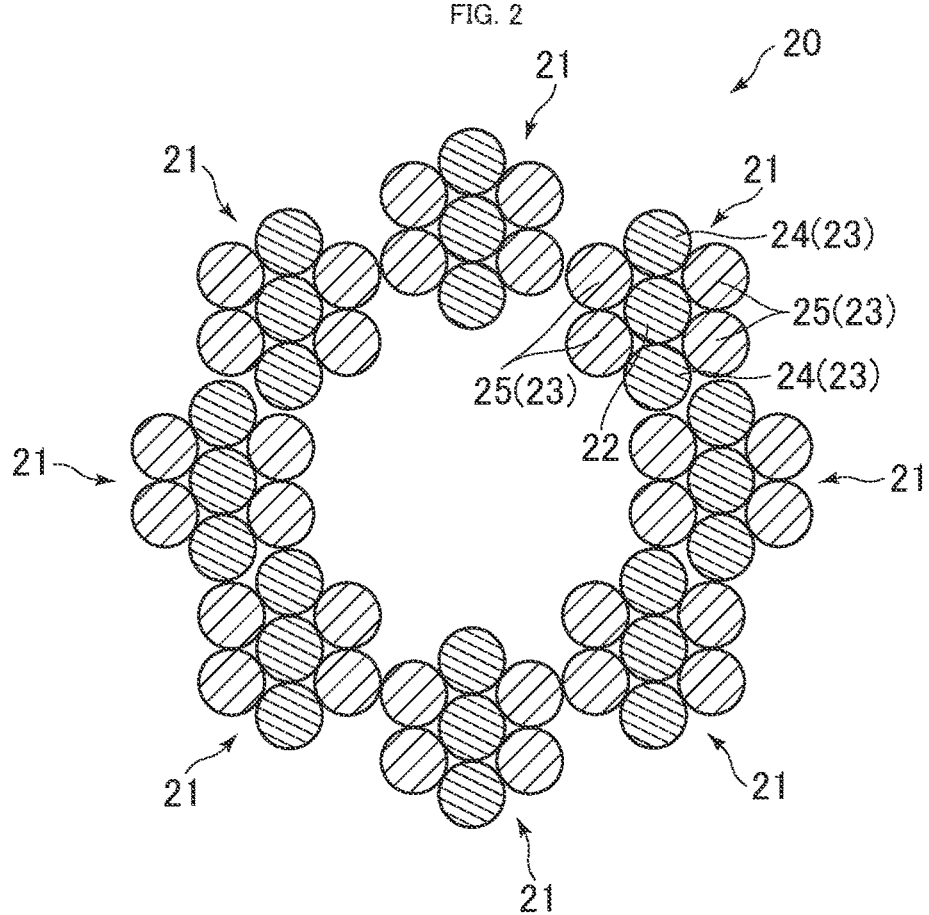
FIG. 2 is a cross-sectional view of the coil body illustrated in FIG. 1 taken along line II-II.
Figure 3:
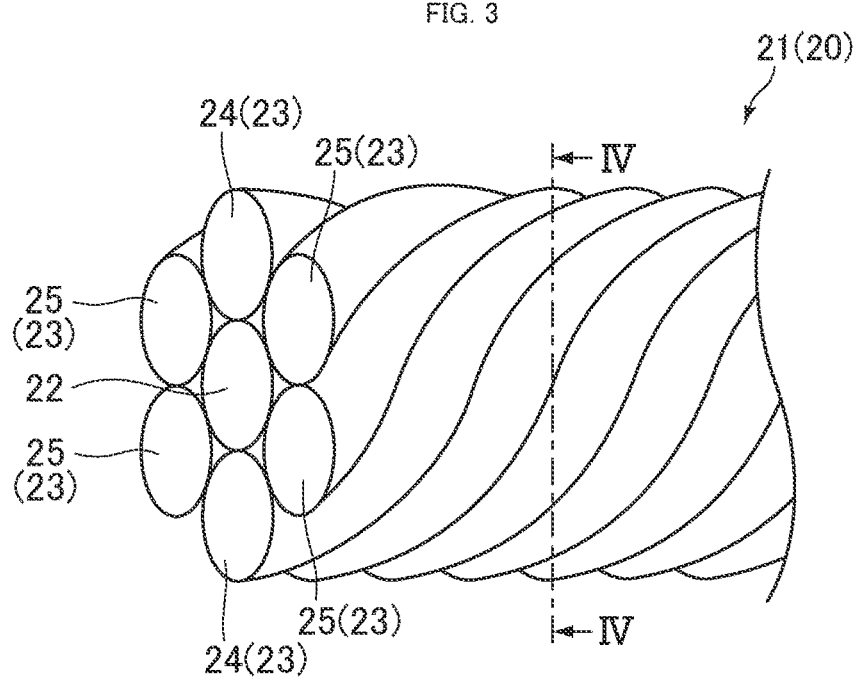
FIG. 3 is a perspective view of a twisted wire according to an embodiment of the present disclosure.
Figure 4:
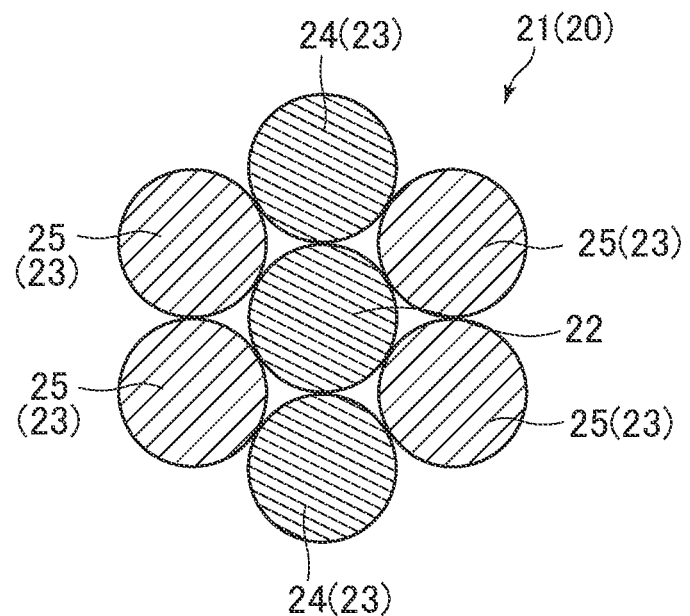
FIG. 4 is a cross-sectional view of the twisted wire illustrated in FIG. 3 taken along line IV-IV.

FIG. 2 illustrates a cross-sectional view of the coil body 20 of the guide wire 1 illustrated in FIG. 1 taken along line II-II. FIG. 3 illustrates a perspective view of a twisted wire 21 forming the coil body 20. FIG. 4 illustrates a cross-sectional view of the twisted wire 21 illustrated in FIG. 3 taken along line IV-IV.

As illustrated in FIG. 1, the coil body 20 is provided so as to cover the outer peripheries of a part of the tapered portion 12 and the distal end portion 13. As illustrated in FIG. 2, the coil body 20 includes the twisted wires 21, and is formed by spirally winding a plurality of such twisted wires 21 (eight in the present embodiment).

As illustrated in FIGS. 3 and 4, the twisted wire 21 includes a core wire 22 and six side wires 23 wound so as to cover the outer periphery of the core wire 22.

As illustrated in FIG. 4, the side wire 23 includes a pair of first side wires 24 that are arranged point-symmetrically around the core wire 22, and four second side wires 25 other than the first side wires 24.

In the present embodiment, the core wire 22 and the first side wire 24 are made of the same first material as the first material forming the core shaft 10. That is, the core wire 22 and the first side wire 24 are made of stainless steel, a superelastic alloy such as a Ni—Ti alloy, or the like. The core wire 22 and the first side wire 24 correspond to the first element wire.

The second side wire 25 is made of a second material that is different from the first material and has a higher melting point than the first material. Examples of the second material include radiopaque materials such as platinum, tungsten, and alloys containing these elements (for example, platinum-nickel alloys). The melting point of stainless steel is about 1400 to 1500° C., the melting point of the Ni—Ti alloy is about 1200 to 1300° C., the melting point of platinum is 1768° C., and the melting point of tungsten is 3422° C. The second side wire 25 corresponds to a plurality of second element wires.

Next, a distal end joint part 30 will be described.

As illustrated in FIG. 1, the distal end joint part 30 joints the distal end of the distal end portion 13 of the core shaft 10 and the distal end of the coil body 20. The distal end joint part 30 is made of the same first material as the first material forming the core wire 22, the first side wire 24, and the core shaft 10, and is continuous from the distal end of the distal end portion 13, the distal end of the core wire 22, and the distal end of the first side wire 24. Moreover, the distal end joint part 30 wraps the distal ends of the plurality of second side wires 25 (2-1 side wire 25A and 2-2 side wire 25B).

The distal end joint part 30 is formed by mutually melting and jointing a part originally located on the distal end side than the distal end portion 13 of the core shaft 10 and a part originally located on the distal end side than the distal ends of the core wire 22 and the first side wire 24 by a TIG welding or the like. Here, such a part is melted at a temperature higher than the melting point of the first material forming the core wire 22, the first side wire 24, and the core shaft 10 and lower than the melting point of the second material forming the second side wires 25. Thus, the distal ends of the second side wires 25 remain in the distal end joint part 30 without melting. As a result, the distal end joint part 30 wraps the distal ends of the plurality of second side wires 25.

Figure 5:
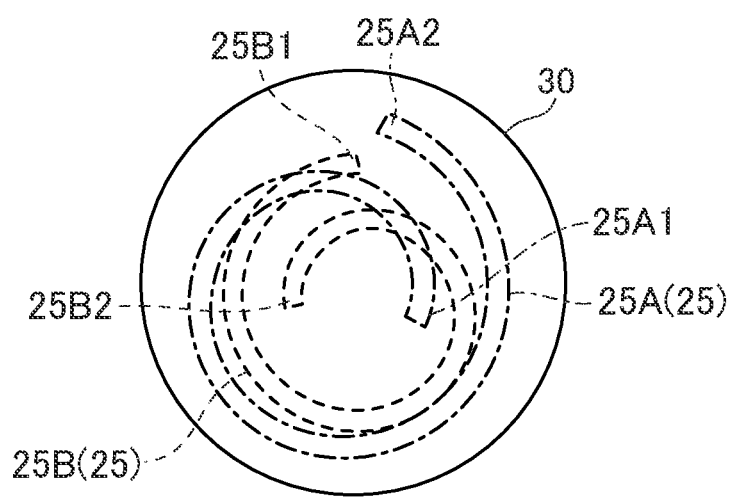
FIG. 5 illustrates a front view of the guide wire according to the embodiment of the present disclosure.

Moreover, the plurality of second side wires 25 includes the 2-1 side wire 25A and the 2-2 side wire 25B. As illustrated in FIGS. 1 and 5, the 2-1 side wire 25A extends spirally at the distal end joint part 30 so as to broaden radially outward toward the distal end, and the 2-2 side wire 25B extends spirally at the distal end joint part 30 so as to narrower radially inward toward the distal end. In FIG. 5, the 2-1 side wire 25A has a proximal end portion 25A1 and a distal end portion 25A2 in the distal end joint part 30, and the 2-2 side wire 25B has a proximal end portion 25B1 and a distal end portion 25B2 in the distal end joint part 30.

As described above, the plurality of second side wires 25 are not gathered in the distal end joint part 30 and extend in a diverged manner. The present embodiment describes only the 2-1 side wire 25A and the 2-2 side wire 25B as the second side wire 25 in the distal end joint part 30. However, the other second side wires 25 also extend in a diverged manner in the distal end joint part 30. The 2-1 side wire 25A corresponds to the 2-1 wire, and the 2-2 side wire 25B corresponds to the 2-2 wire.

Meanwhile, the proximal end of the coil body 20 is fixed to the core shaft 10 by the proximal end fixing part 40. Examples of the material forming the proximal end fixing part 40 include metal brazing such as an Sn—Pb alloy, a Pb—Ag alloy, an Sn—Ag alloy, and an Au—Sn alloy.

Next, the use form of the guide wire 1 will be described. The guide wire 1 is inserted into the blood vessel of the thigh from the distal end joint part 30 and is advanced along the blood vessel to the coronary artery. Next, after the guide wire 1 is advanced to pass a treatment region such as a stenosis of a blood vessel or a false cavity near the CTO, a treatment instrument such as a balloon catheter or a stent is transported along the guide wire 1, so that various treatments are performed at the treatment region. After the treatment is completed, the guide wire 1 is withdrawn from the body by retrograding through the blood vessel, and a series of operations is completed.

The guide wire 1 described above includes the distal end joint part 30 that joints the distal end of the core shaft 10 and the distal end of the coil body 20. The distal end joint part 30 is made of the first material and is continuous from the distal end of the core shaft 10, and the distal ends of the core wire 22 and the first side wire 24 that are the first element wires. The distal end joint part 30 wraps the distal ends of a plurality of second side wires 25 that are the second element wires. In such a configuration, the distal ends of the plurality of second side wires 25 made of the second material are wrapped by the distal end joint part 30 that is continuous from the distal end of the core shaft 10 and the distal ends of the core wire 22 and the first side wire 24 and is made of the same material (first material) as the core shaft 10, the core wire 22, and the first side wire 24. This increases the anchor effect between the distal end joint part 30 and the coil body 20, and improves the joint strength between the distal end joint part 30 and the coil body 20. Therefore, it is possible to prevent the coil body 20 from separating from the distal end joint part 30.

In addition, it is possible to easily form the structure in which the distal end joint part 30 wraps a plurality of second side wires 25 by melting the first material at a temperature higher than the melting point of the first material and lower than the melting point of the second material, because the melting point of the second material is higher than the melting point of the first material.

Further, the 2-1 side wire 25A extends spirally at the distal end joint part 30 so as to increase in diameter toward the distal end, and the 2-2 side wire 25B extends spirally at the distal end joint part 30 so as to reduce in diameter toward the distal end. This further increases the anchor effect between the distal end joint part 30 and the coil body 20, and further improves the joint strength between the distal end joint part 30 and the coil body 20. Therefore, it is possible to further prevent the coil body 20 from separating from the distal end joint part 30.

Note that the present disclosure is not limited to the configurations of the above-described embodiment, but is defined by the terms of the claims and is intended to include any modifications within the scope and meaning equivalent to the terms of the claims.

For example, in the above-described embodiment, the coil body 20 is configured by spirally winding a plurality of twisted wires 21 (eight in the present embodiment). However, it may be formed by spirally winding one twisted wire 21. Moreover, the twisted wire 21 includes the core wire 22, two first side wires 24, and four second side wires 25. That is, the twisted wire 21 includes three first element wires and four second element wires. However, the twisted wire 21 may include at least one first element wire and at least two second element wires. Further, in the above-described embodiment, a plurality of second side wires 25 (the 2-1 side wire 25A and the 2-2 side wire 25B) are not gathered in the distal end joint part 30. However, the present disclosure is not limited thereto. The plurality of second side wires 25 may be gathered in the distal end joint part 30 (in other words, they extend spirally from the coil body 20 toward the distal end direction with a constant outer diameter without increasing or reducing in diameter). Furthermore, it is preferable that the surface roughness of the outer peripheral surface of the plurality of second side wires 25 in the distal end joint part 30 is rougher than the outer peripheral surface of the plurality of second side wires 25 in the coil body 20, although it is not illustrated in the drawings. This further increases the anchor effect between the distal end joint part 30 and the coil body 20, and further improves the joint strength between the distal end joint part 30 and the coil body 20.

REFERENCE SIGNS LIST

1 guide wire
10 core shaft
20 coil body
21 twisted wire
22 core wire
23 side wire
24 first side wire
25 second side wire
25A 2-1 side wire
25B 2-2 side wire
30 distal end joint part

The invention claimed is:

1. A guide wire, comprising:
a core shaft that is made of a first material;
a coil that is provided to cover an outer periphery of the core shaft and is formed by twisting a first wire made of the first material and a plurality of second wires made of a second material different from the first material; and
a distal end joint that joins a distal end of the core shaft and a distal end of the coil, wherein
the distal end joint is made of the first material and is continuous from the distal end of the core shaft and the distal end of the first wire,
the distal end joint wraps the distal ends of the plurality of second wires,
the plurality of second wires include a third wire and a fourth wire, and
the third wire extends spirally at the distal end joint so as to broaden radially outward toward the distal end, and the fourth wire extends spirally at the distal end joint so as to narrower radially inward toward the distal end.

2. The guide wire according to claim 1, wherein a melting point of the second material is higher than a melting point of the first material.

3. The guide wire according to claim 1, wherein the core shaft is tapered so as to reduce in diameter toward the distal end.

4. The guide wire according to claim 1, wherein the first material is stainless steel or Ni—Ti alloy.

5. The guide wire according to claim 1, wherein the coil comprises a plurality of twisted wires, each of the twisted wires being formed by twisting the first wire and the plurality of second wires.

6. The guide wire according to claim 5, wherein the coil comprises eight of the twisted wires.

7. The guide wire according to claim 5, wherein each of the twisted wires is composed of one of the first wire as a core wire, two of the first wire as a part of side wires, and four of the second wire as another part of the side wires.

8. The guide wire according to claim 7, wherein the core wire is surrounded by the first wire, the second wire, the second wire, the first wire, the second wire, and the second wire clockwise.

9. The guide wire according to claim 1, wherein the second material is platinum, tungsten, or alloys containing either platinum or tungsten.

10. The guide wire according to claim 2, wherein the distal end joint is made by melting the distal end of the core shaft and the distal end of the coil at a temperature higher than the melting point of the first material and lower than the melting point of the second material.

* * * * *